United States Patent [19]

Takeuchi et al.

[11] 4,133,753

[45] Jan. 9, 1979

[54] METHOD OF ION EXCHANGE CHROMATOGRAPHY

[75] Inventors: Seiji Takeuchi, Hitachiohta; Kazunori Fujita, Naka, both of Japan

[73] Assignee: Hitachi, Ltd., Japan

[21] Appl. No.: 845,721

[22] Filed: Oct. 26, 1977

[30] Foreign Application Priority Data

Nov. 10, 1976 [JP] Japan .................. 51/135637

[51] Int. Cl.² ............................ B01D 15/08
[52] U.S. Cl. ...................... 260/112.5 R; 210/31 C; 260/326.2; 260/326.27; 548/344; 562/443; 562/445; 562/447; 562/516; 562/554
[58] Field of Search ................ 210/31 C, 198 C; 260/529

[56] References Cited

U.S. PATENT DOCUMENTS

| | | | |
|---|---|---|---|
| 3,537,821 | 11/1970 | Hrdina | 210/31 C |
| 3,686,118 | 8/1972 | Benson | 210/31 C |
| 4,042,327 | 8/1977 | Haney et al. | 210/31 C |

Primary Examiner—John Adee
Attorney, Agent, or Firm—Craig & Antonelli

[57] ABSTRACT

The separation of constituents is carried out in such a way that a mixed amino acid sample is supplied to a separation column packed with a cation exchange resin and that, during the analysis of the single sample, five sorts of elutes of different compositions are supplied to the separation column in succession and by stages. The pH of the elute at the second stage is held higher than that of the elute at the first stage, and the pH's of the elutes at the third to fifth stages are held successively higher. However, the pH of the elute at the third stage is held lower than that of the elute at the second stage. On the other hand, the concentrations of counter ions contained in the elutes at the first to fifth stages are held successively higher inversely to the order in which the elutes are supplied. Notwithstanding that the pH of the elute at the third stage is lowered, the broadening of a component peak can be prevented by the increase of the counter ion concentration. Moreover, the analytical time is shortened as a whole.

12 Claims, 7 Drawing Figures

RETENTION TIME (hours)

RETENTION TIME (hours)

METHOD OF ION EXCHANGE CHROMATOGRAPHY

BACKGROUND OF THE INVENTION

This invention relates to ion exchange chromatography which employs the single-column method. The "single-column method" does not signify that only one separation column exists in a liquid chromatographic analyzer, but it signifies that the separation of components for one sample is executed with one separation column. Accordingly, a case where a plurality of samples are subjected to the separations of components by a plurality of corresponding separation columns in parallel is also covered within the category of the single-column method.

In the past, in separating the constituents of a mixed amino acid sample by the liquid chromatography which exploited an ion exchange resin, individual separation columns for acidic and neutral components and for basic components were used. This method was disadvantageous in that, since the sample needed to be divided in two and then introduced into the two separation columns, the precious sample was wasted.

In 1972, J. R. Benson published that 17 components of amino acids constituting protein were separated by a separation column (American Laboratory: volume 10, page 53). Thereafter, an amino acid analyzer which separates 47 components of amino acids in an organism liquid in 5.5 hours by employing the single-column method has come into the market. In this analyzer, during the analytical cycle of one sample, 5 sorts of elutes of different compositions are successively supplied in change-over.

In the above method for separating the 47 components of the amino acids of the organism liquid, it takes about 160 minutes to separate acidic amino acids and neutral amino acids which total 30 components, and it takes about 170 minutes to subsequently separate basic amino acids which total 17 components. Although this method has shortened the analytical time considerably as compared with the past method, the development of a speedier method of analysis has been desired.

SUMMARY OF THE INVENTION

An object of this invention is to provide a method of ion exchange chromatography according to which, in continuing the separation of components by successively changing-over a plurality of sorts of elutes, the components can be separated more promptly.

This invention is premised on the fact that, during the separation cycle of one sample, a plurality of sorts of elutes are successively supplied to a separation column in change-over. Among the elutes to be successively fed to the separation column, a specific one has its pH-value made equal to or smaller than the pH-value of the elute to be supplied immediately precedently to the specific elute. In addition, the concentrations of counter ions in the plurality of sorts of elutes are made higher inversely to the sequence in which the elutes are supplied.

While a preferred embodiment according to this invention is applied to the analysis of amino acids in an organism liquid, the invention is also applicable to the separations of other samples, for example, a sample of protein constituting amino acids, a sample of nucleotides or organic acids, etc.

In the preferred embodiment according to this invention, five sorts of elutes are employed during the analysis of one sample. Only the elute which is supplied thirdly has a pH-value smaller than that of the elute which is fed directly before it, i. e., which is fed secondly. Regarding the other elutes, the pH-values become gradually larger in the order of supply. The third elute is fed to a separation column at the time when half the number of neutral amino acids has flowed out from the separation column. The third elute greatly affects the separation rate of basic amino acids. In this embodiment, the separation rate of basic amino acids is remarkably enhanced.

DETAILED DESCRIPTION OF THE PREFERRED EMBODIMENT

This invention will now be described as being applied to the analysis of a mixed amino acid sample of an organism liquid by employing five sorts of elutes. A separation column is packed with a strongly acidic cation exchange resin whose degree of bridge making is 8–12%. The five sorts of elutes are successively selected through a change-over valve, and are fed to the separation column by a feed pump. The introduction of the sample into the column is done while the first elute is being fed into the column. Water at a predetermined temperature is fed from a circulating thermostatic oven to the outer periphery of the separation column. Usually, the temperature is changed in several stages. The regulation of the column temperature is not restricted to the above method, but it may be carried out by the dry oven system. To employ the elutes of different compositions by changing-over them in stages intends to better the separation among various amino acids in the sample and to enhance the elution rate. Without employing the elute at the fifth stage, it is possible to cause all the components of amino acids of an organism to elute and flow out. In this case, however, the analytical time which is required for the separation of all the components becomes long. A mixer which is located downstream of the separation column is fed with a ninhydrine reagent solution from a reagent tank at all times. The amino acids which have developed colors while passing through a reactor after coming out of the mixer have the absorbances measured by a photometer which is equipped with a flow cell. The variation of the absorbances is recorded as a chromatogram by a recorder. After the elute at the final stage has been used and the amino acid components in the sample have been perfectly eluted, a regenerative solution is fed to cause the residual liquid in the separation column to flow out. After causing the first-stage elute to flow again and returning the column packing agent to the equilibrium state, a sample solution is introduced again and the next analysis is performed. In the above, the ninhydrine color development process is exploited as the amino acid detecting process. It is also possible to measure the fluorescences of sample components with the fluorescence detecting process and to obtain a chromatogram of the sample.

Heretofore, in case of subjecting a mixed amino acid sample to the separation of constituents by the use of a plurality of elutes, the pH's of the elutes to be successively fed to a separation column have been made gradually higher. The reason why the elutes with their pH-values increased stepwise are employed in the cation exchange chromatography in this manner will now be explained by taking as an example, glycine being one of amino acids.

Figure 1:
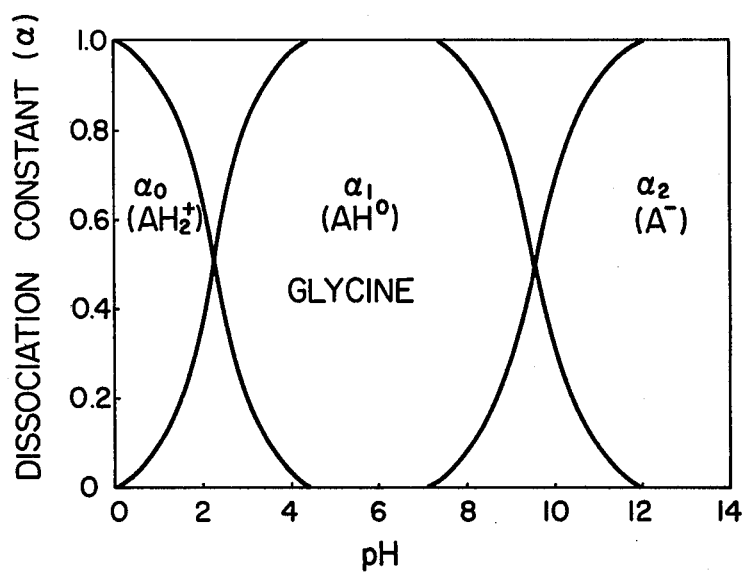
FIG. 1 is a diagram for explaining the dissociation state of glycine.

FIG. 1 is a diagram showing the relationship between the pH-value and the dissociation constant of glycine. The axis of ordinates represents the dissociation constant ($\alpha$), and the axis of abscissas the pH-value. Since amino acids are amphoteric electrolytes, glycine being one of them exists at pH 2 under the state under which more than 50% are cations, at pH 6 under the state under which no charge is present, and at pH 9.5 or above under the state under which more than 50% are anions. By properly selecting the pH-values of elutes, accordingly, various amino acids can be separated in dependence on the differences of the dissociation constants thereof.

Figure 2:
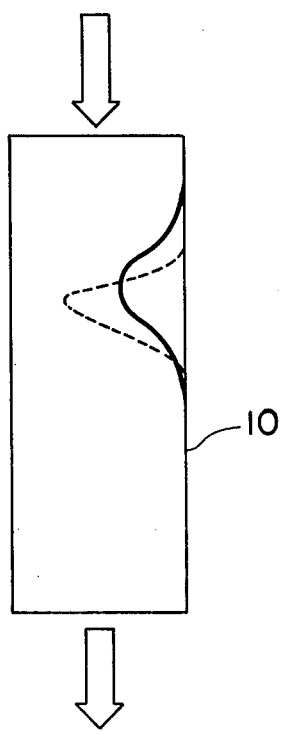
FIGS. 2 and 3 are diagrams for explaining the variation of a component band in a separation column at the time when elutes are changed-over.
Figure 3:
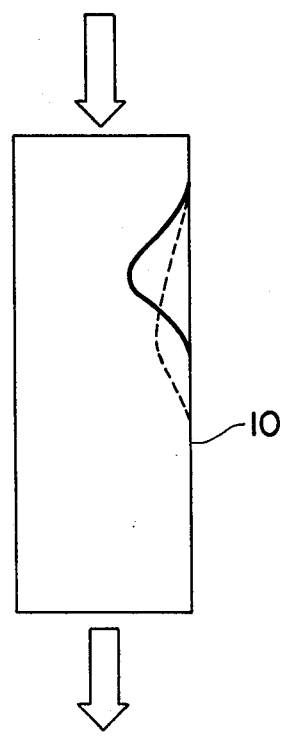

FIGS. 2 and 3 are diagrams for explaining the variations of component bands in a separation column at the time when elutes are changed-over by stages. Let it be supposed that a sample containing only glycine has been already introduced in a separation column 10 and that an elute is flowing in the direction of arrows in each figure. A component peak represented by a solid line indicates the component band of glycine at a first-stage elute. (pH = 3). This component band presents a Gaussian distribution curve. Here, the elute is changed-over to a second-stage elute of a larger pH-value, for example, pH 6. Then, since the elutes are replaced from a hinder part in the moving direction of the band (in the direction of the arrows), the glycine changes from $AH^{+2}$ to $AH^0$ and loses the ion exchangeability. In consequence, the moving speed of the rear side of the component band becomes high, so that the component peak becomes sharp as shown by a broken line in FIG. 2. This phenomenon is generally called the self-sharpening effect. In contrast, if the elute of pH 3 is changed-over to a second-stage elute of pH 2 or so, the rear part of the component band undergoes an increase in the factor of producing $AH^{+2}$ and therefore comes to exhibit an intenser affinity. In consequence, the rear side slows and the component band is expanded as shown in FIG. 3. Accordingly, the component band becomes wider, and the peak height becomes lower. For the reason described thus far, in the stage elution process of the cation exchange chromatography, the successive increases of the pH-values of the elutes has been regarded as being effective to enhance the resolving power and to shorten the analytical time.

The following relation holds between the concentration of counter ions in an elute and the amino acid distribution coefficient Kd of an ion exchange resin phase:

$$Kd = K_M^{A\ H_2} \left( \frac{[\overline{M}]}{[M]} \right) \cdot \frac{1}{1 + k/[H]} \quad (1)$$

where $K_M^{A\ H_2}$ denotes the ion exchange equilibrium constant, and $[\overline{M}]$ and $[M]$ denote the counter ion concentrations of the ion exchange resin phase and the elute phase, R denotes the dissociation constant of amino acids, and [H] denotes concentrations of hydrogen ion respectively. It is understood from Eq. (1) that the distribution coefficient of an amino acid becomes smaller as the counter ion concentration in the elute becomes higher. Accordingly, the elution of the amino acid becomes faster as the concentration becomes higher.

The inventors have noticed this fact, and have made the present invention by considering that the broadening of a component peak will be preventable by properly combining the pH-value and the counter ion concentration of the elute.

Symbols of component peaks of amino acids as appear in various figures, and the names of the corresponding amino acids are collectively indicated in Table 1. Amino acids from phosphoserine 18 to $\beta$-amino-iso-butylic acid 46 are neutral and acidic amino acids, while homocystine and the subsequent amino acids are basic amino acids.

Table 1

| Symbols | Names of amino acids | Symbols | Names of amino acids |
|---|---|---|---|
| 18 | phosphoserine | 40 | iso-leucine |
| 19 | taurine | 41 | leucine |
| 20 | urea | 42 | nor-leucine |
| 21 | aspartic acid | 43 | tyrocine |
| 22 | hydroxy proline | 44 | phenylalanine |
| 23 | threonine | 45 | $\beta$-alanine |
| 24 | serine | 46 | $\beta$-amino-iso-butylio acid |
| 25 | asparagine | 47 | homocystine |
| 26 | glutamic acid | 48 | $\gamma$-amino-iso-butylic acid |
| 27 | glutamine | 49 | tryptophane |
| 28 | sarcocine | 50 | ethanolamine |
| 29 | $\alpha$-amino adipic acid | 51 | ammonia |
| 30 | proline | 52 | d, l-hydroxylysine |
| 31 | glycine | 53 | d, l-hydroxylysine |
| 32 | alanine | 54 | ornitine |
| 33 | citruline | 55 | histidine |
| 34 | $\alpha$-amino-n-butylic acid | 56 | 1-methylhistidine |
| 35 | valine | 57 | lysine |
| 36 | cystine | 58 | 3-methylhistidine |
| 37 | metionine | 59 | anserine |
| 38 | d, l-cystathionine | 60 | carnocine |
| 39 | d, l-cystathionine | 61 | arginine |

In separating a mixed amino acid sample of an organism liquid by employing five sorts of elutes, the counter ion concentration in the third-stage elute was changed as 0.35 M, 0.55 M and 0.80 M. Under these conditions, analytical experiments were conducted. Then, although the analytical time was shortened, the separations of $\beta$-amino-i-butylic acid 46 as well as homocystine 47, ethanolamine 50 to hydroxylysines 52, 53, and histidine 55 to carnocine 60 became inferior at 0.55 M and 0.80 M.

Merely by the increase of the counter ion concentration, accordingly, it is difficult to quicken the analysis without degrading the separation performance.

According to another experiment by the inventors, it has been revealed that, with respect to a combination between a counter ion concentration of 0.35 M and a pH-value of 3.6, the sharpness of a component band does not worsen even when the pH-value is made smaller than 3.6 at a counter ion concentration of 0.80 M.

Figure 4:
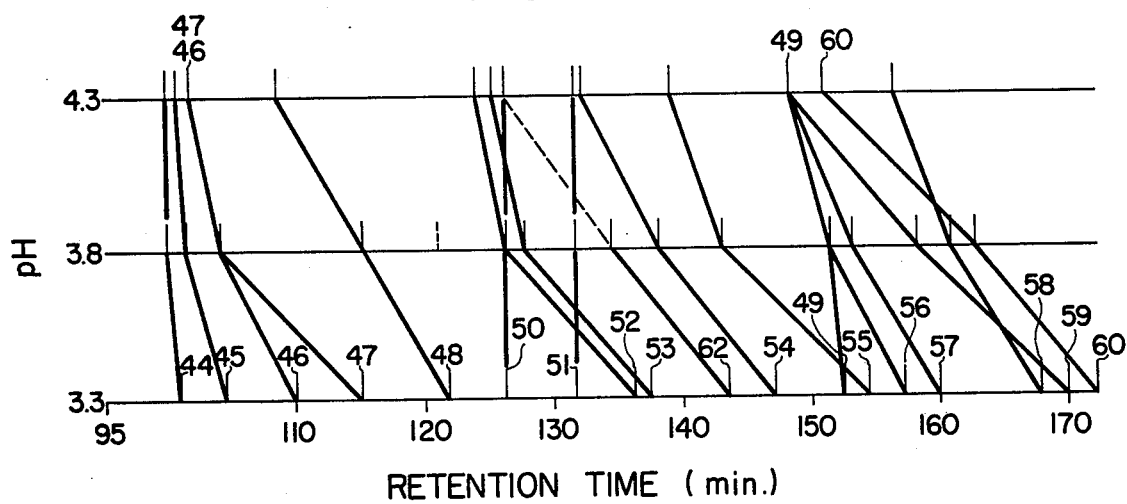
FIG. 4 is a diagram showing the variations of the retention time of amino acids at the time when the pH of that one of five sorts of elutes which is supplied thirdly is changed.

FIG. 4 is a diagram showing the variations of the retention times of various amino acids at the time when the counter ion concentration of the third-stage elute was held at 0.80 M and the pH-value thereof was changed. The axis of ordinates represents the pH-value, while the axis of abscissas represents the retention time in min. The counter ion concentration and the pH-value of the first-stage elute were respectively made 0.15 M and 2.95, and those of the second-stage elute were respectively made 0.25 M and 3.70. Referring to FIG. 4, although some differences are noted between in the case of pH 4.3 and the case of pH 3.8, the separations of β-amino-i-butylic acid 46 as well as homocystine 47 and tryptophane 49 to carnocine 60 are difficult. When the pH is further lowered to 3.3, the general elution time becomes long, but the amino acids from phenylalanine 44 to carnocine 60 can be separated substantially perfectly. The retention time of carnocine 60 at pH 3.3 is 170 minutes odd.

The retention time of carnocine obtained by the method in which the pH's were made successively higher was about 280 minutes. Therefore, the analytical time is sharply shortened in spite of the obtainment of the same extent of separation performance. In this case, the broadening of the component band attributed to making the pH-value of the third-stage elute smaller than that of the second-stage elute was not noted at all, and a sharp component peak in a symmetric form was obtained. That is, the effect owing to the regulation of the counter ion concentration appeared remarkably.

Figure 5:
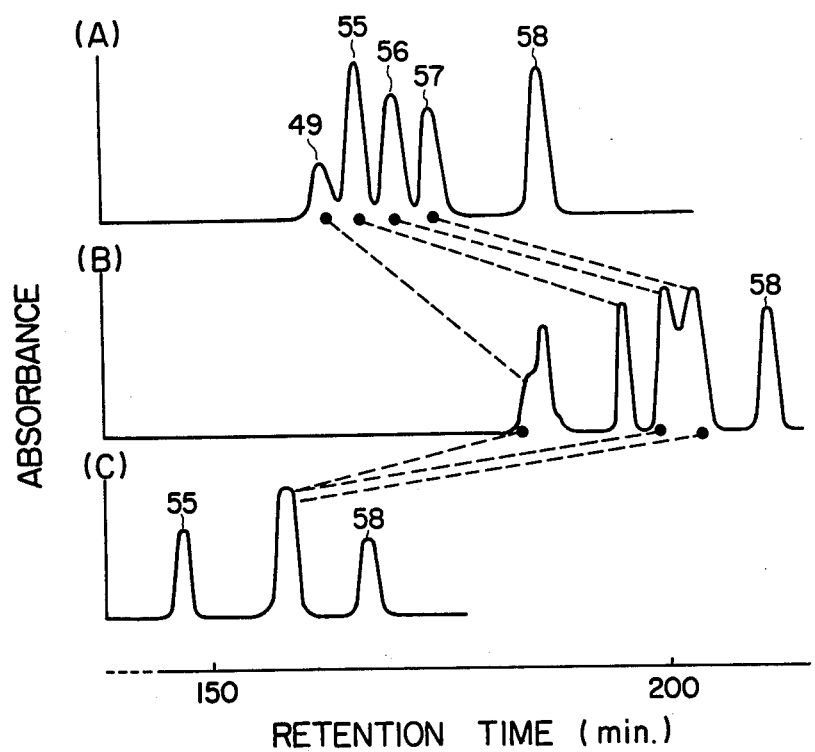
FIG. 5 is a diagram for explaining the separated state of component peaks in a chromatogram.

FIG. 5 shows parts of chromatograms of the experimental results in FIG. 4 in order to compare the separated states of component peaks. (C) in FIG. 5 is the chromatogram at the time when the counter ion concentration and the pH of the third-stage elute were 0.80 M and 4.3 respectively, (B) is the chromatogram at the time when they were 0.40 M and 3.3 respectively, and (A) is the chromatogram at the time when they were 0.80 M and 3.3 respectively. The five components of tryptophane 49, histidine 55, 1-methylhistidine 56, lysine 57 and 3-methylhistidine 58 are perfectly separated in the chromatogram (A), whereas they are not separated in the chromatograms (B) and (C). It is also judged from the recorded chromatograms that, as to the sharpness of the component peaks, (C) is the best, (A) being to the same extent or slightly inferior, (B) being the worst.

EXAMPLE 1

Figure 6:
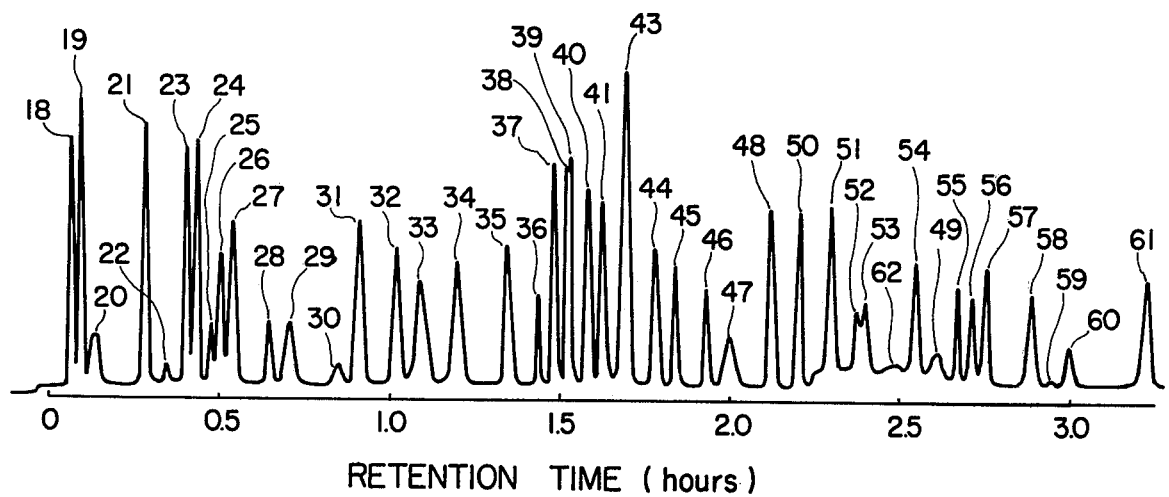
FIG. 6 is a chromatogram showing an example of analysis of amino acids in an organism liquid.

FIG. 6 illustrates an example in which a mixed amino acid sample of an organism liquid was analyzed. In this example, a separation column was packed with a copolymer resin of styrene and divinylbenzene as had a degree of bridge making of 12%. The dimensions of the separation column were 2.6 mm in the inside diameter and 248 mm in the length. The temperature of the separation column was made 40° C.-67° C. The flow rate of each elute was 0.2 ml/min., and the inlet pressure of the separation column was made 100 kg/cm$^2$.

Table 2 indicates five sorts of elutes which were used in this example. In each elute, there were mixed lithium citrate, citric acid, lithium chloride, ethanol, thioglycol and preservatives. In this case, the counter ion concentration indicates the concentration of lithium ions. Instead of lithium citrate, a lithium salt of any other organic acid can be used. In that case, however, the corresponding organic acid is adopted in place of the citric acid. For example, lithium tartrate and tartaric acid are combined, and lithium acetate and acetic acid are combined. Thioglycol is added as an antioxidant for metionine and cystine. Ethanol may be replaced with any other organic alcohol. As the counter ions, sodium ions or potassium ions can be employed instead of the lithium ions (Li$^+$). In case of employing sodium ions or potassium ions, however, the separations of asparagine and glutamine become difficult. pH's were adjusted by varying the composition ratios of the foregoing reagents. As a regenerative solution for regenerating the separation column after separating the components of the sample, a lithium hydroxide solution which contained 0.20 M of lithium ions and whose pH was higher than 12 was employed. Alternatively, potassium hydroxide or sodium hydroxide can be used. The changeover times of the second-, third-, fourth- and fifth-stage elutes were 64 minutes, 90 minutes, 134 minutes and 164 minutes after the initiation of the separation, respectively.

Table 2

| Elutes | pH's | Counter ion concentrations | Ethanol | Thioglycol |
|---|---|---|---|---|
| first-stage | 2.95 | 0.15 M | 4.0 vol % | 0.5 vol % |
| second-stage | 3.70 | 0.25 M | 3.0 vol % | 0.5 vol % |
| third-stage | 3.32 | 0.80 M | 1.5 vol % | 0 |
| fourth-stage | 4.10 | 1.00 M | 0 | 0 |
| fifth-stage | 5.59 | 1.20 M | 0 | 0 |

The reason why, in the chromatogram of FIG. 6, the base line rises from immediately after ethanolamine 50 is that ammonium ions contained in the first- and second-stage elutes and having been concentrated in the separation column are eluted at the time of the third-stage elute. This problem of ammonium ion elution can be eliminated by providing an ammonia cutting filter.

The average elution time per component was approximately 4 minutes as regards the neutral and acidic amino acids, and was approximately 4.5 minutes as regards the basic amino acids. It was sharply improved as compared with the elution time in the case of FIG. 2.

The addition of ethanol to the first-stage elute serves to better the separations of threonine 23 and serine 24. The addition of the same to the second- and third-stage elutes serves to selectively move amino acids of intense adsorptivity. When benzyl alcohol to the extent of 0.1 vol. % is added to the second- and third-stage elutes, the elution of only tryptophane 49 can be promoted.

EXAMPLE 2

Figure 7:
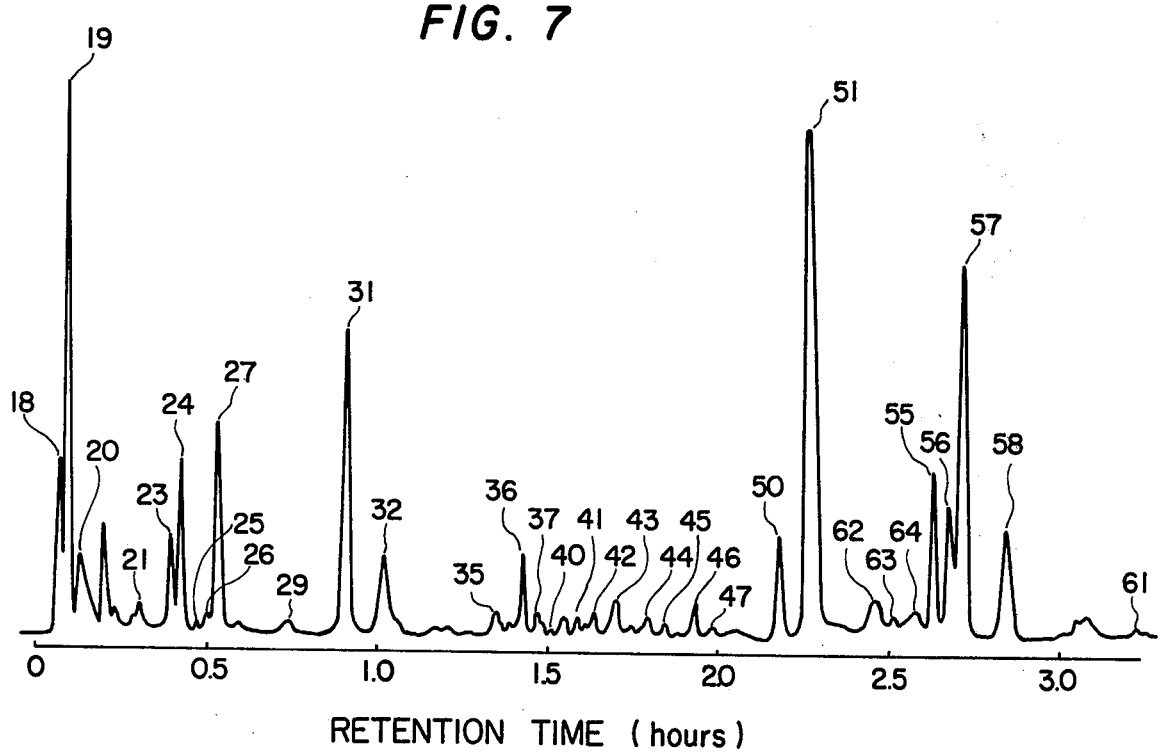
FIG. 7 is a chromatogram showing an example of analysis of human urine.

FIG. 7 shows a chromatogram which was obtained by analyzing human urine under the same measuring conditions as in Example 1. A urine sample used herein was as stated below. After gathering the urine, some toluene was added thereto. The pH was made about 12 by adding caustic soda. Thereafter, the vacuum deaeration was carried out for 6 hours, to strip ammonia. Further, the pH was made about 2 with hydrochloric acid. The resultant sample was introduced by 20 μl without being concentrated, and was analyzed.

Although, in the above examples, the mixed amino acid samples of the organism were analyzed by the five-stage elution, this invention is also applicable to different sorts of samples, and the number of elutes is not restricted to five. Although, in the above examples, the pH of the elute at only one stage was made lower than at the preceding stage, it will also be possible to lower the pH's at two or more stages in accordance with a sample to be analyzed.

The pH's and the counter ion concentrations of elutes for the separation of components of a mixed organism amino acid sample can be adopted within ranges specified in Table 3. The pH of the third-stage elute is usually made lower than that of the second-stage elute. However, even when the pH's of both the elutes are substantially equal, an effect is brought forth.

Table 3

| Elutes | Ranges of pH's | Ranges of counter ion concentrations |
|---|---|---|
| first-stage | 2.7 – 3.3 | 0.1 – 0.3 |
| second-stage | 3.1 – 3.9 | 0.2 – 0.4 |
| third-stage | 3.0 – 3.9 | 0.3 – 1.0 |
| fourth-stage | 3.6 – 4.3 | 0.5 – 1.2 |
| fifth-stage | 4.0 – 12.0 | 0.5 – 1.5 |

What is claimed is:

1. A method for the chromatographic separation of components of an amino acid mixture by means of introducing successively to a column of an ion exchange resin a plurality of sorts of elutes, said elutes containing alkali metal ions, during the separation of components of the amino acid mixture, which method comprises the steps of:
   (1) introducing to the column a first elute having a predetermined pH and a predetermined alkali metal ion concentration,
   (2) introducing to the column a second elute, the pH of which is lower than that of the first elute, and the alkali metal ion concentration of which is higher than that of the first elute, and
   (3) introducing to the column a third elute, the pH of which is higher than that of the first elute, and the alkali metal ion concentration of which is higher than that of the second elute.

2. A method as claimed in claim 1, wherein said second elute is introduced to the column before the basic amino acids are flowed out from the column.

3. A method for the chromatographic separation of organism liquid including amino acids by means of introducing successively to a column of an ion exchange resin a plurality of sorts of elutes, said elutes containing alkali metal ions, during the separation of components of the organism liquid, which method comprises the steps of:
   (1) introducing to the column a first elute having a predetermined pH and a predetermined alkali metal ion concentration,
   (2) introducing to the column a second elute, the pH of which is higher than that of the first elute, and the alkali metal ion concentration of which is higher than that of the first elute,
   (3) introducing to the column a third elute, the pH of which is lower than that of the second elute, and the alkali metal ion concentration of which is higher than that of the second elute, and
   (4) introducing to the column a fourth elute, the pH of which is higher than that of the second elute, and the alkali metal ion concentration of which is higher than that of the third elute.

4. A method as claimed in claim 3, wherein the alkali metal ions are selected from the group consisting of lithium ions, sodium ions, and potassium ions.

5. A method as claimed in claim 3, wherein the first elute has the pH value less than about 3.1 and the fourth elute has the pH value more than about 4.0.

6. A method as claimed in claim 3, wherein said third elute is introduced to the column before the basic amino acids are flowed out from the column.

7. A method as claimed in claim 3, wherein said alkali metal ions comprise lithium ion.

8. A method as claimed in claim 3, wherein the third elute has an alkali metal concentration higher than the average concentration between the second elute and the fourth elute.

9. A method as claimed in claim 3, including introducing to the column a fifth elute, the pH of which is higher than that of the fourth elute, and the alkali metal ion concentration of which is higher than that of the fourth elute.

10. A method as claimed in claim 9, wherein the first elute has a pH between 2.7–3.3 and an alkali metal ion concentration of 0.1–0.3M, the second elute has a pH between 3.1–3.9 and an alkali metal ion concentration of 0.2–0.4M, the third elute has a pH between 3.0–3.9 and an alkali metal ion concentration of 0.3–1.0M, the fourth elute has a pH between 3.6–4.3 and an alkali metal ion concentration of 0.5–1.2M, and the fifth elute has a pH of 4.0–12.0 and an alkali metal ion concentration of 0.5–1.5M.

11. A method as claimed in claim 3, wherein the first elute has a pH between 2.7–3.3 and an alkali metal ion concentration of 0.1–0.3M, the second elute has a pH between 3.1–3.9 and an alkali metal ion concentration of 0.2–0.4M, the third elute has a pH between 3.0–3.9 and an alkali metal ion concentration of 0.3–1.0M, and the fourth elute has a pH between 3.6–4.3 and an alkali metal ion concentration of 0.5–1.2M.

12. A method for the chromatographic separation of components of an amino acid mixture by means of introducing successively to a column of an ion exchange resin a plurality of sorts of elutes, said elutes containing alkali metal ions, during the separation of components of the amino acid mixture, which method comprises the steps of:
   (1) introducing to the column a first elute having a predetermined pH and a predetermined alkali metal ion concentration,
   (2) introducing to the column a second elute, the pH of which is lower than that of the first elute, and the alkali metal ion concentration of which is higher than that of the first elute, wherein the second elute is introduced to the column before the basic amino acids are flowed out from the column, and wherein the second elute has an alkali metal ion concentration sufficiently higher than the concentration of the first elute to cancel the enlarged retention time caused by the lowering of the pH of the second elute, and
   (3) introducing to the column a third elute, the pH of which is higher than that of the first elute, and the alkali metal ion concentration of which is higher than that of the second elute.

* * * * *